(12) United States Patent
Wakatsuki

(10) Patent No.: US 9,631,169 B2
(45) Date of Patent: Apr. 25, 2017

(54) THREE DIMENSIONAL TISSUES FOR HIGH-THROUGHPUT ASSAYS

(75) Inventor: Tetsuro Wakatsuki, Milwaukee, WI (US)

(73) Assignee: INVIVO SCIENCES INC., Madison, WI (US)

(*) Notice: Subject to any disclaimer, the term of this patent is extended or adjusted under 35 U.S.C. 154(b) by 1548 days.

(21) Appl. No.: 12/996,168

(22) PCT Filed: Jun. 5, 2009

(86) PCT No.: PCT/US2009/046431
§ 371 (c)(1),
(2), (4) Date: Jan. 25, 2011

(87) PCT Pub. No.: WO2009/149363
PCT Pub. Date: Dec. 10, 2009

(65) Prior Publication Data
US 2011/0118143 A1    May 19, 2011

Related U.S. Application Data

(60) Provisional application No. 61/059,126, filed on Jun. 5, 2008.

(51) Int. Cl.
| | | |
|---|---|---|
| *G01N 33/50* | (2006.01) |
| *C40B 30/06* | (2006.01) |
| *C12Q 1/02* | (2006.01) |
| *C12M 1/34* | (2006.01) |
| *C12M 1/32* | (2006.01) |
| *C12M 1/12* | (2006.01) |

(52) U.S. Cl.
CPC ............ *C12M 41/46* (2013.01); *C12M 23/12* (2013.01); *C12M 25/14* (2013.01); *C12Q 1/02* (2013.01); *C40B 30/06* (2013.01); *G01N 33/5082* (2013.01)

(58) Field of Classification Search
CPC ...... C12M 41/46; C12M 25/14; C12M 23/12; C12Q 1/02; C40B 30/06; G01N 33/5082
See application file for complete search history.

(56) References Cited

U.S. PATENT DOCUMENTS

| | | |
|---|---|---|
| 4,593,042 A | 6/1986 | Liang |
| 4,705,785 A | 11/1987 | Schwender et al. |
| 4,839,280 A | 6/1989 | Banes |

(Continued)

FOREIGN PATENT DOCUMENTS

| | | |
|---|---|---|
| DE | 19500498 | 7/1996 |
| EP | 1250416 | 5/2006 |

(Continued)

OTHER PUBLICATIONS

AnaSpec ("Detection Reagents & Kits" brochure, 2005, select pages).*

(Continued)

*Primary Examiner* — Jeremy C Flinders
(74) *Attorney, Agent, or Firm* — Michael Best & Friedrich LLP

(57) ABSTRACT

Provided herein are methods of detecting responses of bio-artificial tissues to agents by performing assays using three-dimensional bio-artificial tissues. The methods are adaptable to high-throughput platforms.

23 Claims, 9 Drawing Sheets

(56) References Cited

U.S. PATENT DOCUMENTS

| | | | |
|---|---|---|---|
| 4,940,853 | A | 7/1990 | Vandenburgh |
| 5,038,795 | A | 8/1991 | Roush et al. |
| 5,326,357 | A | 7/1994 | Kandel |
| 5,464,853 | A | 11/1995 | Chan et al. |
| 5,571,083 | A | 11/1996 | Lemelson |
| 5,665,391 | A | 9/1997 | Lea |
| 5,706,815 | A | 1/1998 | Sarvazyan et al. |
| 5,843,766 | A | 12/1998 | Applegate et al. |
| 6,197,575 | B1 | 3/2001 | Griffith et al. |
| 6,332,364 | B1 | 12/2001 | Buschmann |
| 6,881,584 | B1 | 4/2005 | Lenhard et al. |
| 7,449,306 | B2 | 11/2008 | Elson et al. |
| 8,227,240 | B2 | 7/2012 | Elson et al. |
| 2003/0064358 | A1 | 4/2003 | Elson et al. |
| 2003/0091979 | A1 | 5/2003 | Eschenhagen |
| 2005/0147959 | A1* | 7/2005 | Frondoza et al. ............ 435/2 |
| 2006/0105357 | A1 | 5/2006 | Benesch et al. |
| 2008/0038812 | A1 | 2/2008 | Elson et al. |
| 2009/0068701 | A1 | 3/2009 | Elson et al. |

FOREIGN PATENT DOCUMENTS

| | | |
|---|---|---|
| JP | 2007515158 | 6/2007 |
| WO | WO 90/00595 | 1/1990 |
| WO | 98/38490 | 9/1998 |
| WO | 00/69355 | 11/2000 |
| WO | 01/11340 | 2/2001 |
| WO | WO 01/55297 | 8/2001 |
| WO | WO 03/016860 | 2/2003 |
| WO | 2005/039396 | 5/2005 |
| WO | 2008/047723 | 4/2008 |

OTHER PUBLICATIONS

United States Patent Office Action for U.S. Appl. No. 11/774,393 dated Jan. 20, 2012 (21 pages).
Japanese Patent Office Action for Application No. 2011-512695 dated Jan. 14, 2014 (6 pages, English translation included).
United States Patent Office Notice of Allowance for U.S. Appl. No. 11/774,393 dated Mar. 23, 2012 (9 pages).
Chinese Patent Office Action for Application No. 200980128485.X dated Aug. 4, 2013 (10 pages—English Translation).
Allen, F.D. et al., "Calpain regulated cell adhesion in EGF-stimulated fibroblast-populated-collagen-lattice contraction," BED (American Society of Mechanical Engineers), 50 (Proceedings of the Bioengineering Conference, Jun. 27-Jul. 1, 2001), 353-354.
Dewolf, C. et al., "Interaction of dystrophin fragments with model membranes," Biophys. J. (1997) 72:2599-2604.
Eschenhagen, T. et al., "Transfection studies using a new cardiac 3D gel system," Molecular Approaches to Heart Failure Therapy, Hasenfuss et al. eds., Verlag Gmbh & Co., Germany (2000) 144-156.
Eschenhagen, T. et al., "Three-dimensional reconstitution of embryonic cardiomyocytes in a collagen matrix: a new heart muscle model system," FASEB J. (1997) 11(8):683-694.
Fink, C. et al., "Chronic stretch of engineered heart tissue induces hypertrophy and functional improvement," FASEB J. (2000) 14(5):669-679.
Floyd Jr., S.S. et al., "Ex vivo gene transfer using adenovirus-mediated full-length dystrophin delivery to dystrophic muscles," Gene Therapy (1998) 5:19-30.
Kolodney, M.S. et al., "Correlation of myosin light chain phosphorylation with isometric contraction of fibroblasts," J. Biol. Chem. (1993) 268(32):23850-23855.
Kolodney, M.S. et al., "Isometric contraction by fibroblasts and endothelial cells in tissue culture: a quantitative study," J. Cell Biol. (1992) 117(1):73-82.
Pasternak, C. et al., "Mechanical function of dystrophin in muscle cells," J. Cell Biol. (1995) 128(3):355-361.
Paul, R.J. et al., "Effects of microtubule disruption on force, velocity, stiffness and [Ca2+] in porcine coronary arteries," Am. J. Physiol. Heart Circ. Physiol. (2000) 279:H2493-H2501.
Petersen, N.W. et al., "Dependence of locally measured cellular deformability on position on the cell, temperature, and cytochalasin B," Proc. Natl. Acad. Sci. USA (1982) 79:5327-5331.
Shen, X. et al., "Pharmacological modulation of the mechanical response of airway smooth muscle to length oscillation," J. Appl. Physiol. (1997) 83(3):739-745.
Sundberg, S.A., "High-throughput and ultra-high-throughput screening: solution- and cell-based approaches," Curr. Opin. Biotechnol. (2000) 11:47-53.
Takakuda, K. et al., "Strengthening of fibrous tissues under mechanical stimuli (in vitro experiments)," JSME Int. J. Ser. A. (1998) 41:576-583.
Wakatsuki, T. et al., "Phenotypic screening for pharmaceuticals using tissue constructs," Curr. Pharm. Biotech. (2004) 5(2):181-189.
Wakatsuki et al., "Cell mechanics studied by a reconsituted model tissue," Biophys. J. (2000) 79:2353-2368.
Wakatsuki, T. et al, "Effects of cytochalasin D and latrunculin B on mechanical properties of cells," J. Cell Science (2001) 114(5):1025-1036.
Website for Webster's Third International Dictionary, unabridged, www.lionreference.chadwyck.com, 6 pages; retrieved on Sep. 19, 2006.
Zahalak, G.I. et al., "Determination of cellular mechanical properties by cell poking, with an application to leukocytes," J. Biomech. Engin. (1990) 112:283-294.
Zimmerman, W.H. et al., "Three-dimensional engineered heart tissue from neonatal rat cardiac myocytes," Biotech. Bioeng. (2000) 68(1):106-114.
Canadian Patent Office Action for Application No. 2,497,343 dated Feb. 11, 2010 (3 pages).
European Patent Office Search Report for Application No. 02752832.2 dated Feb. 22, 2005 (3 pages).
European Patent Office Action for Application No. 02752832.2 dated Sep. 16, 2005 (4 pages).
European Patent Office Action for Application No. 02752832.2 dated Apr. 4, 2007 (4 pages).
European Patent Office Action for Application No. 02752832.2 dated Mar. 10, 2008 (4 pages).
European Patent Office Action for Application No. 02752832.2 dated Jul. 24, 2008 (5 pages).
European Patent Office Action for Application No. 08009189.5 dated Sep. 22, 2008 (8 pages).
European Patent Office Action for Application No. 08009189.5 dated Mar. 23, 2010 (4 pages).
European Patent Office Action for Application No. 08009189.5 dated Oct. 13, 2010 (4 pages).
Japanese Patent Office Action for Application No. 2003-521318 dated Mar. 17, 2009 (10 pages) with English translation.
Japanese Patent Office Action for Application No. 2003-521318 dated Jun. 10, 2008 (5 pages) with translation.
Japanese Patent Office Action for Application No. 2003-521318 dated Apr. 6, 2010 (4 pages) English translation only.
International Search Report for PCT/US02/25761 dated Apr. 21, 2003 (5 pages).
Written Opinion for PCT/US02/25761 dated Aug. 5, 2004 (6 pages).
International Preliminary Report on Patentability for PCT/US02/25761 dated Feb. 17, 2005 (6 pages).
International Search Report and Written Opinion for Application No. PCT/US2009/46431 dated Aug. 28, 2009 (8 pages).
United States Office Action for U.S. Appl. No. 10/219,097 dated Dec. 14, 2005 (13 pages).
United States Office Action for U.S. Appl. No. 10/219,097 dated Sep. 29, 2006 (9 pages).
United States Office Action for U.S. Appl. No. 10/219,097 dated Oct. 9, 2007 (8 pages).
United States Office Action for U.S. Appl. No. 10/219,097 dated Apr. 8, 2008 (5 pages).
United States Patent Office Action for U.S. Appl. No. 11/774,393 dated Dec. 4, 2009 (10 pages).

(56) References Cited

OTHER PUBLICATIONS

United States Patent Office Action for U.S. Appl. No. 11/774,393 dated Aug. 24, 2010 (13 pages).
United States Patent Office Action for U.S. Appl. No. 11/774,393 dated Jan. 31, 2011 (17 pages).
United States Patent Office Action for U.S. Appl. No. 11/774,393 dated Apr. 12, 2011 (17 pages).
United States Patent Office Action for U.S. Appl. No. 12/268,783 dated Sep. 2, 2010 (7 pages).
United States Patent Office Action for U.S. Appl. No. 12/268,783 dated Feb. 15, 2011 (6 pages).
United States Patent Office Notice of Allowance for U.S. Appl. No. 12/268,783 dated Apr. 28, 2011 (5 pages).
Chinese Patent Office Action for Application No. 200980128485.X dated May 7, 2014 (11 pages, English translation included).
Bilsland, J. et al., "A rapid method for semi-quantitative analysis of neurite outgrowth from chick DRG explants using image analysis," J. Neurosci. Meth. (1999) 92:75-85.
Canadian Patent Office Action for Application No. 2,497,343 dated Nov. 23, 2011 (3 pages).
European Patent Office Action for Application No. 09759521.9 dated Oct. 6, 2011 (8 pages).
Chinese Patent Office Action for Application No. 200980128485.X dated Jan. 17, 2013 (9 pages—Original and English Translation).
European Patent Office Action for Application No. 09759521.9 dated Sep. 30, 2014 (4 pages).
Chinese Patent Office Action for Application No. 200980128485.X dated Nov. 17, 2014 (11 pages, English translation included).
Examiner's Report from the Canadian Intellectual Property Office for Application No. 2,726,979 dated Apr. 29, 2016 (4 pages).
Canadian Patent Office Action for Application No. 2,726,979 dated Apr. 17, 2015 (3 pages).

\* cited by examiner

Scaffold (20)

A.

B.

C.

US 9,631,169 B2

THREE DIMENSIONAL TISSUES FOR HIGH-THROUGHPUT ASSAYS

CROSS-REFERENCE TO RELATED APPLICATIONS

This application is a national stage filing under 35 U.S.C. 371 of International Application No. PCT/US2009/046431, filed Jun. 5, 2009, which claims the benefit of priority of U.S. Provisional Patent Application No. 61/059,126, filed Jun. 5, 2008, both of which are incorporated herein by reference in their entirety.

STATEMENT REGARDING FEDERALLY SPONSORED RESEARCH

This invention was made with government support under R41 grant number AT003984 awarded by the NIH/NCCAM, and under R44 grant number GM087784 awarded by the NIH. The United States government has certain rights in the invention.

INTRODUCTION

The need to characterize the diverse bio-molecules in living cells during normal development as well as in disease states has driven the development of cell-based assays. High throughput cell-based assays now form the foundation of biomedical research. These assays are used in both basic research, such as discovery of cellular components and processes, and applied research, such as drug development. For example, cell-based assays have been developed for monitoring cellular activities and functions such as cell viability, cell proliferation, gene expression, and intra- and intercellular signaling. Such assays are useful for high throughput (HTP) screening applications. However, many cell-based assays are not adaptable to high throughput screening because detection sensitivities or signal strengths are too low. In addition, high throughput cell-based assays are routinely performed on cells in a monolayer and these assays do not adequately portray the behavior of cells in a tissue. There is a need for increased sensitivity and increased signal strength such that cell-based assays can be adapted to high throughput applications.

SUMMARY

High throughput cellular assay systems using a three dimensional tissue model and methods of performing such assays are provided herein. The assays are useful for monitoring the response of the tissue to treatment with a variety of agents and stressors. Three-dimensional tissues are formed on a scaffold positioned within a well in a multi-well plate. The tissues are suspended above the bottom of the well. An assay is performed on the suspended tissue and the output of the assay is measured in the well.

In one aspect, methods of detecting the response of a tissue to an agent are provided herein. The methods include contacting a bio-artificial tissue with an agent, performing an assay which produces an indicator using the bio-artificial tissue, and detecting a level of the indicator in the well. The level of the indicator is indicative of the response of the bio-artificial tissue to the agent. The bio-artificial tissue used in the assay comprises cells and extracellular matrix and is formed on a scaffold support without a fastener to facilitate tissue adhesion. The scaffold support is positioned above the bottom of a well.

The output of the assay may be a colorimetric or fluorescent product, and the accumulation of the product may be measured using a plate reader. Exemplary assays that may be carried out with the systems in accordance with the invention include, but are not limited to, cell proliferation assays, cell death assays, apoptosis assays, protein expression assays, gene expression assays, enzymatic assays, signaling assays such as kinase activity assays, Ca2+ signaling assays and GPCR signaling assays, assays to assess mitochondrial activity, and extracellular matrix degradation assays.

BRIEF DESCRIPTION OF THE DRAWINGS

The invention may be better understood by reference to the detailed description of specific embodiments in conjunction with the accompanying drawings.

FIG. 2a is a top elevation view of the scaffolds. FIG. 2b is a side elevation view of the scaffold. FIG. 2c is a side elevation view of one way of connecting several scaffolds to each other for ease of use in high throughput applications.

FIG. 5(A) is a photograph of The Palpator™. The system includes an isometric force transducer (a), probe baths (b), and a hydrogel tissue construct (HTC) stage (c) on a temperature regulator plate (d). FIG. 5(B) is a photograph showing the x-y-z motion robotic arm which positions the force transducer with attached probe above the HTCs and lowers the probe onto the tissue for force measurement. FIG. 5(C) is a schematic of the robotic arm with attached force transducer and probe. FIG. 5(D) is a photograph of the probe positioned 1 mm above the mid-plane of a HTC (a) and then lowered until it first touches (b) and then stretches (c) the tissue. FIG. 5(E) is a graph showing representative forces recorded during HTC indentation. Arrows a, b, and c show force measurements associated with probe positions shown in (D). FIG. 5(h) is a graph showing that Cytochalasin D treatment reduced cellular F-actin. HTCs treated with drugs for 24 hours were fixed and labeled with Alexa 568 conjugated phalloidin. Fluorescence intensity was read on a plate reader and plotted relative to control, media treated, HTCs ($I_c$). Data show mean and SEM of 3 replicates; @p<0.02 by Student's t-test vs. controls (Ctrl). FIG. 5(i-w) are micrographs showing REF monolayers treated with medium (i,n,s), CD (j,o,t), RKI1 (k,p,u), DNP (l,q,v), and ROT (m,r,w). At 3 hr (i-m) and 24 hr (n-r, s-w) post treatment, representative monolayers were fixed and stained with Alexa 568 conjugated phalloidin and DAPI. CD caused extensive actin depolymerization by 3 hr (j). RKI1, DNP, and ROT had limited to no effects. CD and ROT induced cytotoxicity was evident by cell shrinkage (g, i, and j), binucleation (l), and nuclear disintegration (O). Note the larger scale bar in (g) and (l). Images were captured on a Leica SP5 confocal microscope using a water-immersion 63× objective, scale bar=50 μm.

FIG. 6(a) is a graph showing that DNP's uncoupling effects were not quantifiable in cell monolayers using a plate reader. Mean and SEM shown, n=11. FIG. 6(b) is a graph showing that the same effects were quantifiable in HTCs. Mean and SEM shown, n=4. FIG. 6(c) is a graph showing a representative tracing of microscopically quantified TMRE signal in REF monolayers treated with DNP. FIG. 6(d) is a graph showing a representative tracing of microscopically quantified TMRE signal in the bottom cell layer of a HTC treated with DNP. Reductions in TMRE signal were higher in magnitude as compared to results from cell layers from HTCs, (c).

FIG. 7(a) is a graph showing that CD and ROT exhibited dose-dependent cytotoxicity. Viability of drug treated HTCs was determined by MTT assay at 24 hours. Absorbance of formazan (converted from MTT in viable cells) was read on a plate reader and expressed relative to control, medium treated, HTCs ($A_C$). 10% DMSO treatment was used as a positive control for this assay which yielded $A/A_C$ of $0.11 \pm 9 \times 10^{-3}$ (not shown in graph); Z-factor>0.85 for control vs. 10% DMSO analysis. Data show mean and SEM of predominately 4, with several 2 and 3, replicates. FIG. 7(b) is a work flow schematic of HTC screening. Duration indicates the amount of time needed to process each plate of HTCs. HTCs are synthesized and allowed to contract for 48 hours prior to use. Shaded parallelograms indicate points of data acquisition. Repeated measurements are possible for in situ indicators, e.g. TMRE. End-point assays, e.g. MTT, require the sacrifice of the HTCs and are carried out at the end of the experiment.

DETAILED DESCRIPTION

Figure 1:
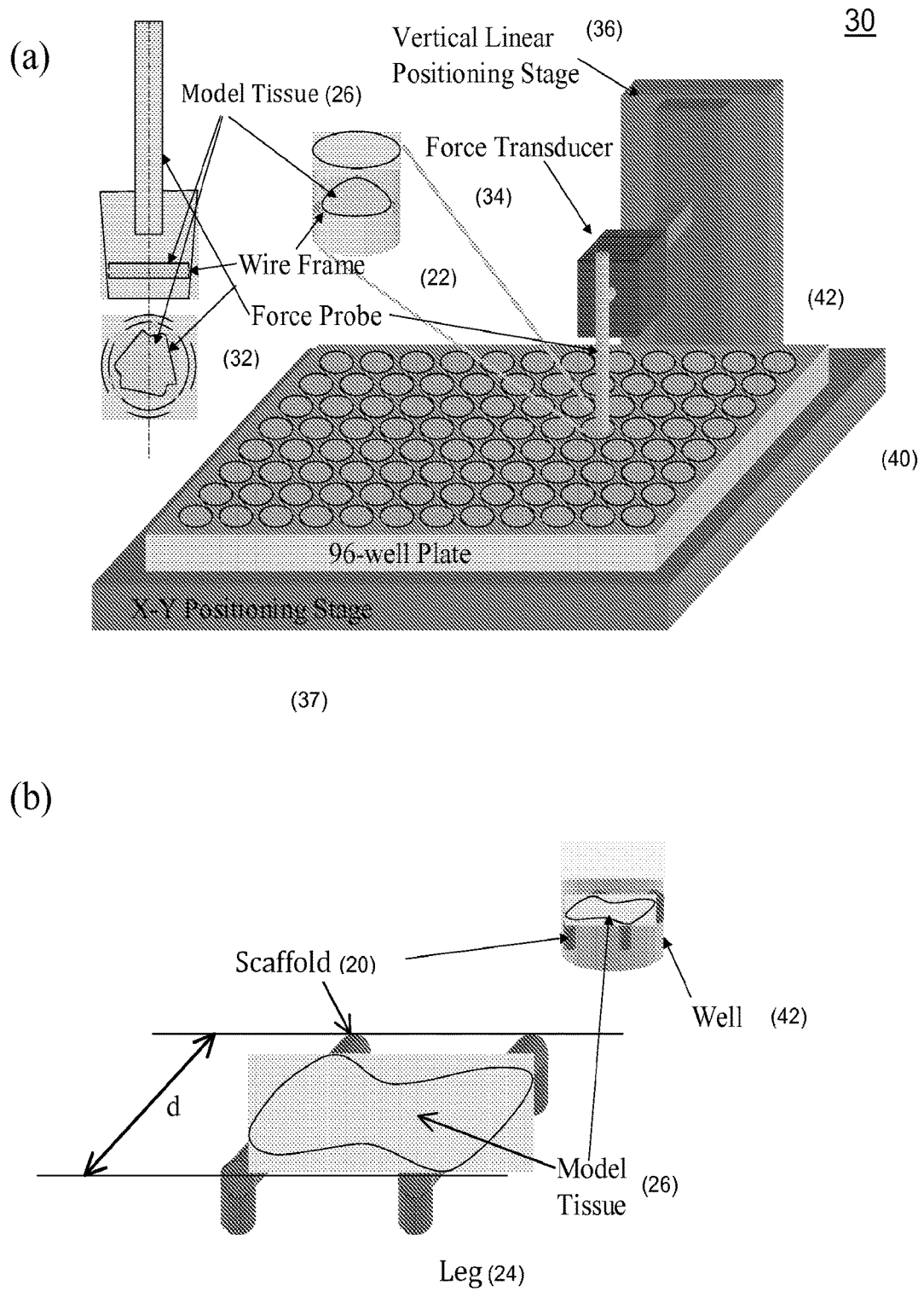
FIG. 1a shows a high throughput system illustrating use of triangular and rectangular (alternative shape) scaffolds shown in FIG. 1b, made of stainless steel wire about one millimeter in diameter, which provide supports upon which reconstituted three dimensional tissues form.

The usefulness of many of the available cell-based high throughput screening assays has been limited due to the low signal strength generated by colorimetric or fluorescent indicators. Such assays generally use cells in a monolayer or suspension culture, rather than cells present in a tissue. In addition, monolayers and suspended cells do not necessarily behave like cells in vivo in the three-dimensional environment of a tissue. The assays and tissues presented here allow these high throughput assays to be performed in a tissue-based system which more closely resembles an in vivo setting. In addition, due to the higher number of cells present in a three-dimensional tissue as compared to a cell monolayer in the same area, the signal generated as an output by an assay on a three-dimensional tissue is amplified.

The invention improves the efficiencies of measuring cell physiology for assays using optical detection systems (such as spectrophotometric and fluorescence plate readers). This is an additional feature of a physiology profiling system using tissues, such as engineered or bio-artificial tissues. As previously described in U.S. Pat. No. 7,449,306, engineered tissues (bio-artificial tissues) may be constructed in miniaturized format, including a 96 well plate format. For example, cells growing in the engineered tissues (3D tissue organoids) may be loaded with fluorescent probes that serve to report on the physiology of intra- and/or extra-cellular activities. The fluorescence probes report the physiological states by changing their intensities or shifting their emission spectra.

Methods of detecting the response of a tissue to an agent are provided herein. The methods include contacting a bio-artificial tissue with an agent, performing an assay that produces an indicator on the bio-artificial tissue, and detecting the level of the indicator in the well. The level of the indicator is indicative of the response of the bio-artificial tissue to the agent. The bio-artificial tissue used in the assay comprises cells and extracellular matrix and is formed on a scaffold support without a fastener to facilitate tissue adhesion. The assays may be adapted for high throughput screening methods.

The bio-artificial tissue may be contacted with an agent via any means available to those skilled in the art. For example, the agent may be added to a well containing the bio-artificial tissue or may be provided to the cells prior to forming the bio-artificial tissue. Alternatively, the agent may be brought into contact with the cells by means of a vector, such as a viral vector or liposome, or via receptor-mediated targeting.

Bioartificial tissue models can be used to assess quantitatively and rapidly the effects of many different classes of agents, including but not limited to, pharmaceuticals or potential pharmaceuticals, toxins, chemicals, nucleic acids, peptides, polypeptides and microorganisms, including pathogens or vectors. For example, agents useful as activators include, but are not limited to, fetal bovine serum (FBS), lysophosphatidic Acid (LPA); thrombin, growth factors including epidermal growth factor (EGF), platelet derived growth factor (PDGF), angotensin-II, endothelin-1, vasopressin and combinations thereof. Inhibitors include, but are not limited to, inhibitors which bind cell surface receptors including a receptor antagonist for angiotensin II receptor and also inhibitors that act within the cell. Inhibitors useful herein include, but are not limited to, those which inhibit signal transduction pathways including genistein, herbimycin and agents which act on the cytoskeleton. Inhibitors also include, but are not limited to, cytochalasin D, latrunclin B, paclitoxol, nocodazole, calyculin A, butane-dione-monoxime (BDM) and combinations thereof.

The amount of agent(s) provided to the bio-artificial tissue is an amount effective to elicit a response from or by a tissue model. An effective amount is generally between about 1 nM to 100 mM, suitably 100 nM to 1 mM, more suitably 500 nM to 500 μM.

After treatment with an agent, an assay can be performed on the bio-artificial tissue. Any assay which can be designed to produce an indicator, such as a colorimetric, fluorescent or radioactive indicator, can be adapted for use with the 3D bio-artificial tissues in accordance with the invention. Assays including but not limited to cell proliferation assays, cell death assays, apoptosis assays, protein expression assays, gene expression assays, enzymatic assays, signaling assays such as kinase activity assays, Ca2+ signaling assays and GPCR signaling assays, assays to assess mitochondrial activity, and extracellular matrix degradation assays may be used in the methods described herein. Assays developed for use with monolayers of cells, in particular those dependent upon uptake of agents or assay reagents by cells, will require longer incubation times in order to allow the agents and assay reagents to be taken up by the cells within the bio-artificial tissue. Assay reagent concentrations will also require adjustment.

Finally, the level of the indicator produced by the assay is detected. The level of indicator produced refers to the output of the assay or the signal resulting from performance of the assay. The level may relate to an amount of indicator produced or an alteration in the indicator itself, for example a change in emission spectra, or uptake of a labeled indicator by the cells. The level of the indicator is indicative of the response of the bio-artificial tissue to the agent. Detection of the level of the indicator may make use of microscopes, optical or fluorescent plate readers or scintillators, dependent on the indicator and assay chosen. The sensitivity of signals detected by microscopes is higher than that of plate readers. Microscopes focus on a cell layer to collect optical signals very efficiently (the detection volume is focused and small). Plate readers use a diffused (unfocused) optical beam (e.g., unfocused laser) to detect molecules in a large volume illuminated by the beam. In conventional cell culture systems, the plate reader measures optical signals from a single cell layer. However, cells in the engineered tissues form at least 5-10 layers, therefore the plate reader can measure a large number of cells at once resulting in optical signals detected by the plate readers that are amplified at least 5-10 fold. See FIG. 4. Plate readers can read signals much faster because they do not require focusing on individual cells, therefore use of plate readers is suitable for high throughput applications. The analyses of images taken by microscopes are also more time-consuming than those taken using a plate reader.

Conventional cell-based assays for measuring cell physiology often use image analysis. Images are generally captured by an automated microscope and analyzed by image-analysis software. Treatments and assays measuring the effects of treatments must be assessed by collecting data from several hundred cells. A statistical variance of data obtained from a single cell is too high to predict average effects of any treatments. To obtain statistically significant data, data from, at a minimum, several hundred cells must be collected.

A plate reader can be used to obtain the same information (e.g. Ca concentration), but the signal is much weaker than that obtained by the automated microscope. One solution to this problem is to increase the number of cells measured by the plate readers. Cells form multiple layers in the engineered 3D tissues, therefore the plate reader can measure more cells in the same area.

Plate readers are superior to microscopes for analyzing the dynamic properties of live-cells. Improved signals and high statistical significance of measurements using the tissue constructs as disclosed herein will allow application of many small scale assays to cell-based high content analysis. Currently microscopes are generally used due to the increased sensitivity, but the methods described herein will allow plate readers to be used for cell-based high content analysis.

Reference is now made to FIGS. 1a and 1b in which a scaffold 20 is shown, suitably including a frame 22, e.g., a triangular frame. A reconstituted tissue 26 forms on scaffold 20. In this illustrated embodiment, wells 42 are slightly tapered toward the bottom and are wells of a 96-well plate 40. The scaffold 20 is securely positioned above the bottom of each well 42, suitably about 1 mm. A non-polymerized solution of collagen containing cells and appropriate cell culture media as described is poured into the wells, filling them to a level 3 mm above the bottom of the well (FIG. 1a). The 96-well plate 40 may be incubated at 37° C. with 5% $CO_2$. During incubation, the cells self-assemble into the bio-artificial tissue 26 and compress the collagen matrix by squeezing out liquid thereby reducing the total volume by about ten fold. Without scaffold 20, the reconstituted or bio-artificial tissue contracts into a small sphere floating in the tissue culture medium.

Scaffolds 20 are suitably made of any non-porous, biocompatible material, such as metal, nonmetal, or plastic. In the Examples, the scaffold was made of stainless steel. One of skill in the art will appreciate that other materials including, but not limited to, glass, polypropylene or polystyrene may also be suitably used to produce the scaffold.

Figure 2:
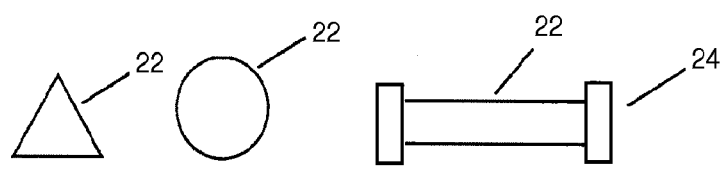
FIG. 2 shows several views of the scaffold.
Figure 2:
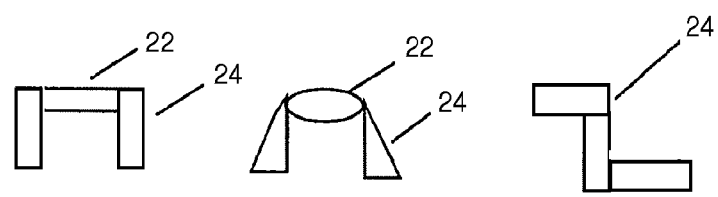
Figure 2:
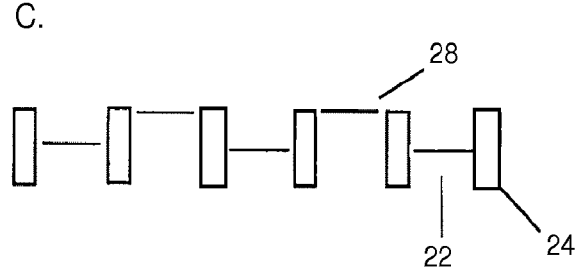

Frame 22 is suitably supported above the bottom 43 of well 42. Frame 22 may be supported by the side of the well by using tissue culture plates 40 with tapered wells. Alternatively, frame 22 may be supported above the bottom of well 42 by using specially designed plates 40 with built-in scaffolds attached to the side of the well or with wells having ledges on which frame 22 rests. In another alternative embodiment, scaffold 20 may include at least one leg 24 attached to frame 22 to support the frame above the bottom of the well. The number of legs 24 required to support the frame will vary depending on the shape of the frame. FIG. 1b depicts scaffold 20 with 4 legs, but scaffolds may be designed with fewer or more legs as depicted in FIG. 2. Legs 24 may be used to support frames 22 by projecting down from the frame and touching the bottom of well 42 or legs 24 may project upwards from frame 22 and support the frame of scaffold 20 by anchoring the scaffold to the top 45 of well 42. For example, leg 24 may have a small hook structure at the end that allows scaffold 20 to hang from the top of the well (FIG. 2(b)). Although frame 22 of scaffold 20 is suitably supported above the bottom of well 42, the exact distance is not critical as long as the tissue can be bathed in media. Suitably, frame 22 is at least about 0.25 mm above the bottom of the well, more suitably the frame is at least about 0.5 or 1.0 mm above the bottom of the well.

Scaffold 20 may take a wide array of shapes. The collagen-containing matrix can be compressed into different shapes using different scaffold shapes such as a circle or rectangle as depicted in FIG. 2. Other scaffold shapes, such as those shown in FIG. 1b and FIG. 2, produced tissue strips with different widths and shapes. Any shape scaffold 20 can be used, including but not limited to, circular, rectangular, triangular, pentagonal, hexagonal, or other higher order polygons. The scaffold may also be formed of more than one member. For example, scaffold 22 may be formed of two parallel members spaced apart with or without one or more perpendicular member connecting them (FIG. 1b and FIG. 2).

In accordance with embodiments of the invention, cells self-assemble to form a tissue model conforming to the shape of the scaffold, i.e., support, for example a wire frame. In forming, the tissue overlays the members of the scaffold and spans the space between the members. For example, on a triangular scaffold, the cells form a membrane spanning among the three edges, which is illustrated in FIG. 1a. The scaffold in the Examples was made of members having about 1 mm cross-sectional diameter, but scaffolds may suitably have smaller or larger cross-sectional diameters. Suitably, the scaffold is made up of one or more members with cross-sectional diameters between about 100 µm and about 2 mm. The scaffold is comprised of generally cylindrical or tubular members that allow the tissue to form around the members such that the tissue overlays the members. The members comprising the scaffold are suitably somewhat rounded to minimize ripping of the tissue when a force is applied. For example, members with a rectangular cross-section could be utilized if the edges were rounded such that the tissue did not tear when force was applied. The members are suitably made of a non-porous material and have a cross-sectional diameter of less than about 2 mm, suitably about 1 mm.

Figure 3:
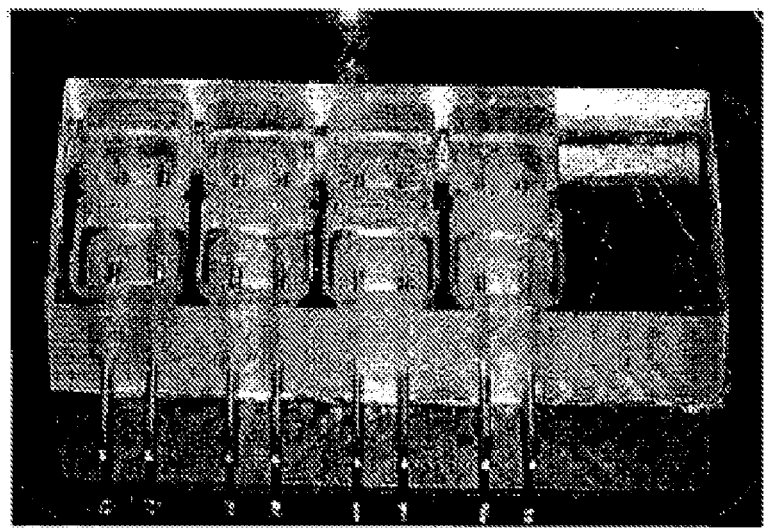
FIG. 3 is a photograph showing a typical engineered three-dimensional tissue.

The bio-artificial tissue forms a membrane structure spanning a horizontal cross-sectional space between or across the members comprising the scaffold. The horizontal cross-sectional space that the bio-artificial tissue spans is suitably larger than 10 µm, but can be as large as the well 42 allows, suitably the tissue spans a space between about 100 µm and about 5 mm, more suitably between 1 mm and 4 mm. A typical bio-artificial tissue depicted in FIG. 3 is approximately 4×4×0.8 mm and formed in an 8 mm×8 mm square chamber. (The shape of chamber was modified for viewing the sample. The tissue was fixed with formaldehyde (10%) and stained with orange dye for clear viewing).

FIG. 3 depicts a prototype multi-well plate 40 comprising scaffolds 20. In the illustrated embodiment, an 8-well plate was machined from a polycarbonate bar (25×60×10 mm) using a tabletop CNC mill (Sherline Products Inc., Vista, Calif.). The 8 square wells 42 of 8×8 mm contained 2 stainless steel bars that make the frame 22 (1 mm diameter). The centers of the stainless steel bars were located 2 mm above the bottom of the well and 2 mm from the side of the well such that the 2 bars were 4 mm apart. A microscope coverslip (No. 1 thickness, Fisherbrand) was used to seal the bottom of each well using silicon glue (Dow Chemical Co., Midland, Mich.) to facilitate microscopic imaging.

For ease of use in a high throughput system using a multi-well plate format, scaffolds 20 may be joined together by a connector 28 in groups including but not limited to, 2, 4, 8, 12 or 96 scaffolds as depicted in FIG. 2C. By joining scaffolds 20 together in groups, the scaffolds can be readily positioned in a multi-well plate 40. Connectors 28 may be made to be readily separable, e.g., such that a quick tugging motion will break the connection and allow the user to customize the number of scaffolds used. The scaffolds and bio-artificial tissue system described herein may also be adopted for use by one of skill in the art in any multi-well plate, including but not limited to, 6 well, 8 well, 12 well, 24 well, 48 well, 192 well or 384 well plates.

As seen in the Examples below, a porous support material, or other fastener, such as a Velcro fastener, is not needed to facilitate tissue adhesion even to the non-porous stainless steel surfaces of the wire frame used. The collagen was compressed to a greater extent at the outer portion of the membrane or tissue strip and allowed the tissue to be suspended on the scaffold without the need for a fastener. Therefore, this outer portion of the membrane can withstand the stress produced by the cells and prevents ripping the bio-artificial tissue off from the wire frame.

Figure 4:
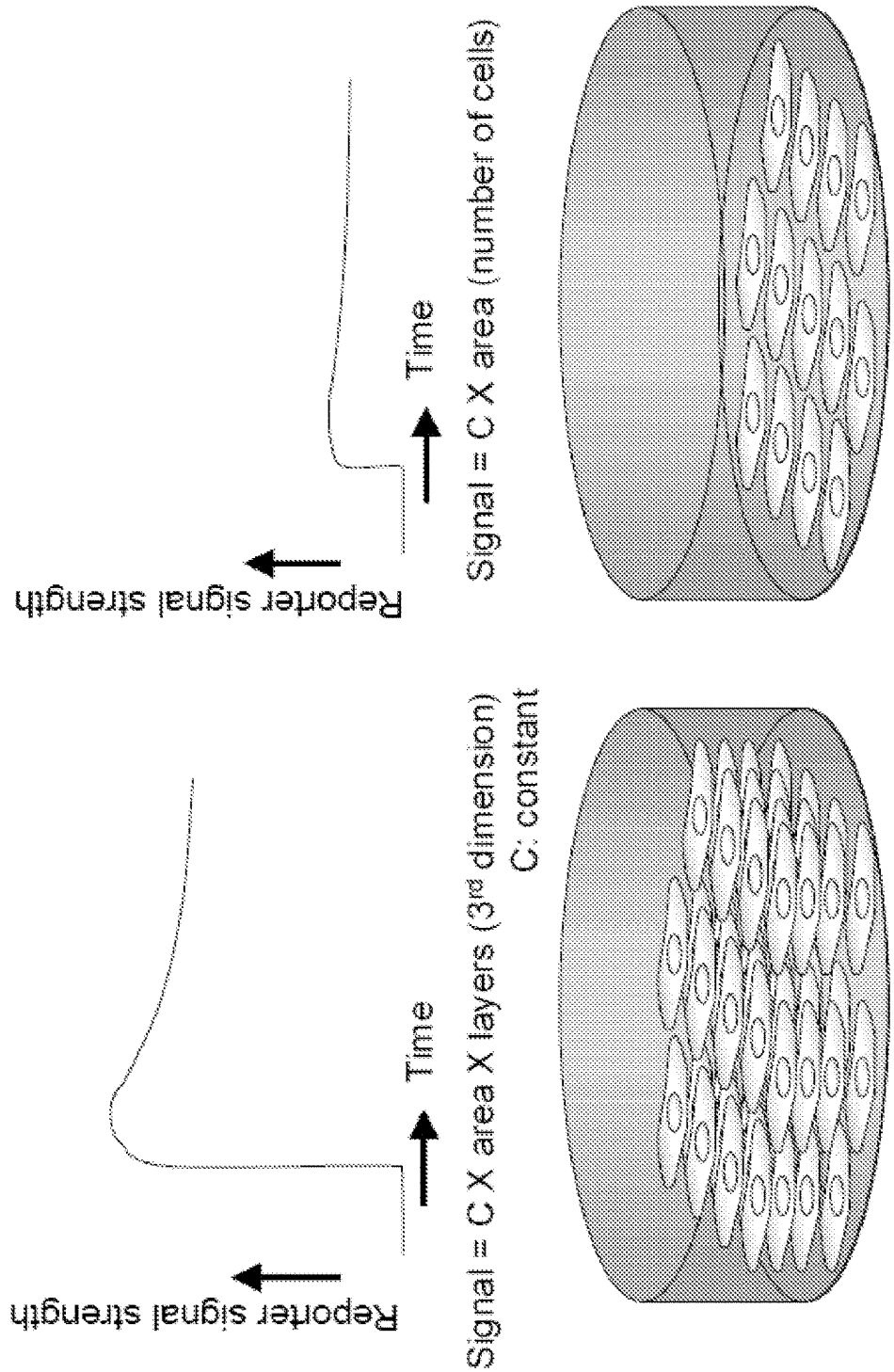
FIG. 4 is a diagram depicting the distinction between a three dimensional tissue and a monolayer of cells. The graphs demonstrate the increased cell-based assay signal strength that may be realized by using a three-dimensional tissue instead of a cellular monolayer.

As illustrated in FIG. 4, the bio-artificial tissue in accordance with several embodiments of the invention provides a three-dimensional tissue which is more akin to an in vivo setting than the cell monolayers of current cell-based assays. The increased cell numbers result in increased signal output for a specific test assay. The invention thus provides a mechanism by which all manner of cell-based assays can be successfully generated in a high throughput system. In addition, unlike other three-dimensional tissues the tissue here is not grown on a mesh or frame which then interferes with optical measurement. Instead the tissue spans the frame and optical measurements are possible.

The system of the invention not only uses smaller amounts of reagents due to the small size of the tissues required for testing, but also allows analysis of tissues maintained in tissue culture conditions, including maintenance of constant temperature and sterile conditions throughout the assay procedure. For example, assays may be performed in a laminar flow hood to avoid contamination of the bio-artificial tissues. In addition, the cells within the tissue are stable such that the assays can be repeated on the same set of bio-artificial tissues several times over the course of hours, days, or even weeks.

Multi-well plate 40 may be a specially designed plate comprising scaffolds 20 for holding the bio-artificial tissues or suitably may be a generally commercially available tissue culture multi-well plate to which scaffolds may be added. The number of wells per plate may vary. Typically plates with between 2 and 1000 wells will be used, suitably plates with between 50 and 500 wells will be used.

The cells used to form the bio-artificial tissues may include, but are not limited to muscle cells, endothelial cells, epithelial cells, fibroblasts, embryonic stem cells, mesenchymal stem cells and cardiac cells. The bio-artificial tissue may comprise cells and collagen or cells and extracellular matrix. Collagens useful in formation of bio-artificial tissues include collagen Classes 1-4 which include all Types I-XIII and combinations thereof. Various types of extracellular matrix may also be used in formation of bio-artificial tissues, such as hydrogels or Matrigel®.

The cells in the reconstituted tissue models in accordance with several embodiments of the invention are in an environment that resembles their condition in natural tissues and organs. Therefore, results of the assays using this method yield results similar to those obtained using animal models. It is contemplated that some of the animal testing can be replaced by using tissue models in accordance with the invention. For example, some tests of agents acting on skin can be conducted using artificial living tissues.

EXAMPLES

Methods

A triangular frame made of stainless steel wire 1 mm in diameter was employed as a scaffold on which the reconstituted tissue formed. The wells are slightly tapered toward the bottom and the frame is securely positioned 1 mm above the bottom of the well (FIG. 1a). A non-polymerized solution of collagen containing cells and appropriate cell culture media was poured into the wells filling the wells to a level 3 mm above the bottom (FIGS. 1b and 3). The 8-well plate in FIG. 3 was incubated at 37° C. with 5% $CO_2$. During the incubation, cells compressed collagen matrices by squeezing liquid out from the porous collagen matrix. Without the wire frame, the reconstituted tissue contracted into a small sphere floating in the tissue culture medium. It was discovered that by utilizing different shapes of wire frames the collagen matrix was compressed into shapes corresponding to shapes of the frames. Illustratively, a triangular wire frame made a membrane spanning among the three edges as shown in FIG. 1a. Other wire frame shapes, such as one shown in FIG. 1b, produced tissue strips with different widths. A porous support material such as a Velcro fastener was not required to facilitate tissue adhesion even to the non-porous stainless steel surfaces of a wire. The collagen was compressed to a greater extent at the outer portion of the membrane or strip. Therefore, this outer portion of the membrane can withstand stress produced by the cells and prevented it from ripping the membrane off the wire frame.

Cell Culture and HTC Formation

Rat embryonic fibroblasts (REF-52) were cultured in Dulbecco's Modified Eagle's Medium (DMEM, MT10013CM, Fisher Scientific, Pittsburgh, Pa.) supplemented with 10% fetal bovine serum (FBS, S11050, Atlanta Biologicals, Lawrenceville, Ga.). Cells were sub-cultured every two to three days. To make hydrogel tissue constructs (HTCs), REF-52 cells (between passages 40 to 70) were dissociated from culture plates by treating with 0.05% trypsin (MT-25-025-CI, Fisher Scientific) for 10 to 15 min. The cells were then centrifuged at 1000 g for 10 min. The trypsin solution was decanted and the cell pellet was re-suspended in 10% FBS DMEM medium. This cell suspension was diluted in HTC tissue solution to achieve a final concentration of $8 \times 10^5$ cells per ml. The HTC tissue solution consisted of 10% FBS DMEM, 1 mg/ml of type 1 collagen (354249, BD Biosciences, San Jose, Calif.) in 0.02 N acetic acid, sufficient sodium hydroxide to neutralize the acid in the collagen, and sufficient 5×DMEM to compensate for the volume of collagen and NaOH. To prevent premature collagen polymerization, the HTC tissue solution was kept on ice until its distribution into our custom-made tissue molds (FIG. 3). Each mold contains 8 separate HTC-forming wells with two built-in horizontal support bars. Three hundred microliters of the HTC tissue solution was aliquoted into each well in these molds and then incubated for 30 min at 37° C. and 5% $CO_2$. After the incubation period, 350 ml of 10% FBS DMEM medium was added to each well and the molds were further incubated for 48 hr. In this time, the solution contracted to form HTCs that span the support bars in the wells.

HTC Force Measurement

The Palpator™ (as described in U.S. Pat. No. 7,449,306, which is incorporated herein by reference in its entirety) was used to quantify the contractility of the HTCs. The molds were placed on the stage of the Palpator™ which automatically inserted a probe into each well and stretched the individual HTC. The probe was connected to a force transducer which measured the resistance force induced in the HTC in response to stretch and exported the values to a computer for recording. A custom Matlab algorithm was used to process and analyze the force data to report a numerical parameter that is indicative of the active cell force in the HTC. To obtain stable measurements of the HTC contractile force, it was necessary to precondition the HTCs by stretching three times prior to actual force measurement. Preconditioning was not necessary if subsequent force measurements were within 30 min of the previous stretch. HTCs at 24 hr post treatment were always pre-conditioned before force measurement.

HTC TMRE Labeling and MTT Assay

The ethyl ester of tetramethylrhodamine (TMRE, T-669, Invitrogen, Carlsbad, Calif.) was used to quantify the mitochondrial potential of the HTCs. HTCs were incubated in 100 nM TMRE for 30 min and then in phenol red free 10% FBS DMEM for 60 min. Phenol red free medium was used to prevent interference with TMRE fluorescence reading. Following labeling, HTCs were preconditioned with three stretches and then prior to background force measurement. HTC TMRE signal was then read on a Synergy HT plate reader (Biotek Instruments, Winooski, Vt.). A custom made adapter plate was used to position the tissue molds on the plate-holding rack of the plate reader. Fluorescence signal was read from the bottom using the 543/590 excitation/emission filter set and a gain setting of 50. TMRE fluorescence intensity was also read following each force measurement at predetermined time points after drug treatments.

3-(4,5-dimethylthiazol-2-yl)-2,5-diphenyltetrazolium (MTT, M-6494, Invitrogen) was used to quantify cell viability in the HTCs. At predetermined times following drug exposure, MTT was added to each well to achieve 0.5 mg/ml. MTT was left in the wells for 2 hr and then removed. The formazan dye that forms in the cells were then suspended in 500 μl of isopropanol (S77795, Fisher Scientific) containing 0.1 N hydrochloric acid. Two hundred microliters of the formazan solution is then put into a 96-well plate well and read on the Synergy HT plate reader. Absorbance at 570 and 650 nm were recorded and the difference ($A_{570}$-$A_{650}$) was used as the absorbance intensity of the formazan.

HTC Drug Treatment

All chemicals are from Sigma (Sigma-Alrich, St. Louis, Mo.) unless otherwise noted. Cytochalasin D (CD, C8273), rotenone (ROT, R8875), 2,4-dinitrophenol (DNP, D198501), and Rho kinase inhibitor 1 (RKI1, 555550, Calbiochem, Gibbstown, N.J.) were suspended in dimethyl sulfoxide (DMSO, D4540) for storage. Stock solution of CD, ROT, and RKI1 were at 1 mM which are serially diluted to 100, 10 and 1 μM in DMEM without phenol red, FBS, glucose, or pyruvate (−F/P/G). DNP was diluted to 1 M in DMSO and then to 100, 10, and 1 mM in −F/G/P DMEM. Following HTC preconditioning and background force (i.e. pre-drug) measurement, 50 μl of the appropriate drug dilutions were added to each well to achieve the desired treatment concentration. Fifty microliters of −F/G/P DMEM was added to the control wells. Upon drug addition, medium in the wells was mixed by pipetting four times.

REF-52 Cell Treatment and Fixing

REF-52 cells were plated on 35 mm culture dishes (50,000 cells) in 10% FBS medium (2 ml). Cells are incubated over night and then treated with compounds. Concentrated CD, RKI1, DNP, and ROT were dissolved in −F/G/P medium and then diluted 10× into each plate of cells (220 μl per 2 ml medium). Cells were incubated with drugs for 24 hours prior to fixing. To fix, treated cells were rinsed once with 2 ml of phosphate buffered saline (PBS, D5652) and then incubated in 1 ml of 4% paraformaldehyde (Sigma) solution (in PBS) for 30 min. Fixed cells are rinsed twice and then stored in 2 ml of PBS.

REF-52 Labeling and Imaging

Fixed REF-52 cells were permeabilized by incubating in 1 ml of 0.1% Triton (BP151, Fisher Scientific) solution (in PBS) for 15 min. Permeabilized cells were rinsed twice with 1 ml TBST buffer and then blocked with 1 ml of 5% goat serum in TBST for 1 hour. One milliliter of 1:200 diluted Alexa 568 conjugated phalloidin (A12380, Invitrogen) in TBST with 2% goat serum was then added to the cells. This staining solution also contained 400 nM of DAPI (D9564). Cells were stained for 30 min and then rinsed twice with TBST. Labeled cells were mounted with Vectashield (Vector Laboratories, Burlingame, Calif.), covered with a cover slide and then sealed with nail polish. The plate was then inverted on to a Leica SP5 confocal microscope (Leica Microsystems, Bannockburn, Ill.) and imaged with 63× water immersion objective. Alexa 568 was excited using the 543 laser line and DAPI was excited using a MaiTai multi-photon laser.

Statistic Analysis

Student's t-test was used to test the reduction of fluorescence signal in CD treated versus control HTCs (FIG. 1h). The Z-factor was used to evaluate the signal-to-noise ratio of the Palpator (FIGS. 1f and 1g), TMRE (FIGS. 2a and 2b), and MTT (FIG. 3a) assays. In the MTT assay, 10% DMSO was used as a positive control.

Results

To measure cellular mechanics for compound screening, we developed a technique to fabricate miniaturized hydrogel tissue constructs (HTCs) and a high-throughput screening system, the Palpator™ (FIG. 5a, 5b, 5c), to quantify the tissues' mechanical properties. The 3D HTCs provides a more natural microenvironment and the cells can better mimic in vivo morphology and physiology. Further, the self-supporting HTCs can be stretched using a force probe for measuring cellular mechanics (FIG. 6d). Using this system, the HTCs' mechanical properties can be quantitatively measured (FIG. 6e) without cell labeling, sophisticated microscopy, or image analysis.

Figure 5:
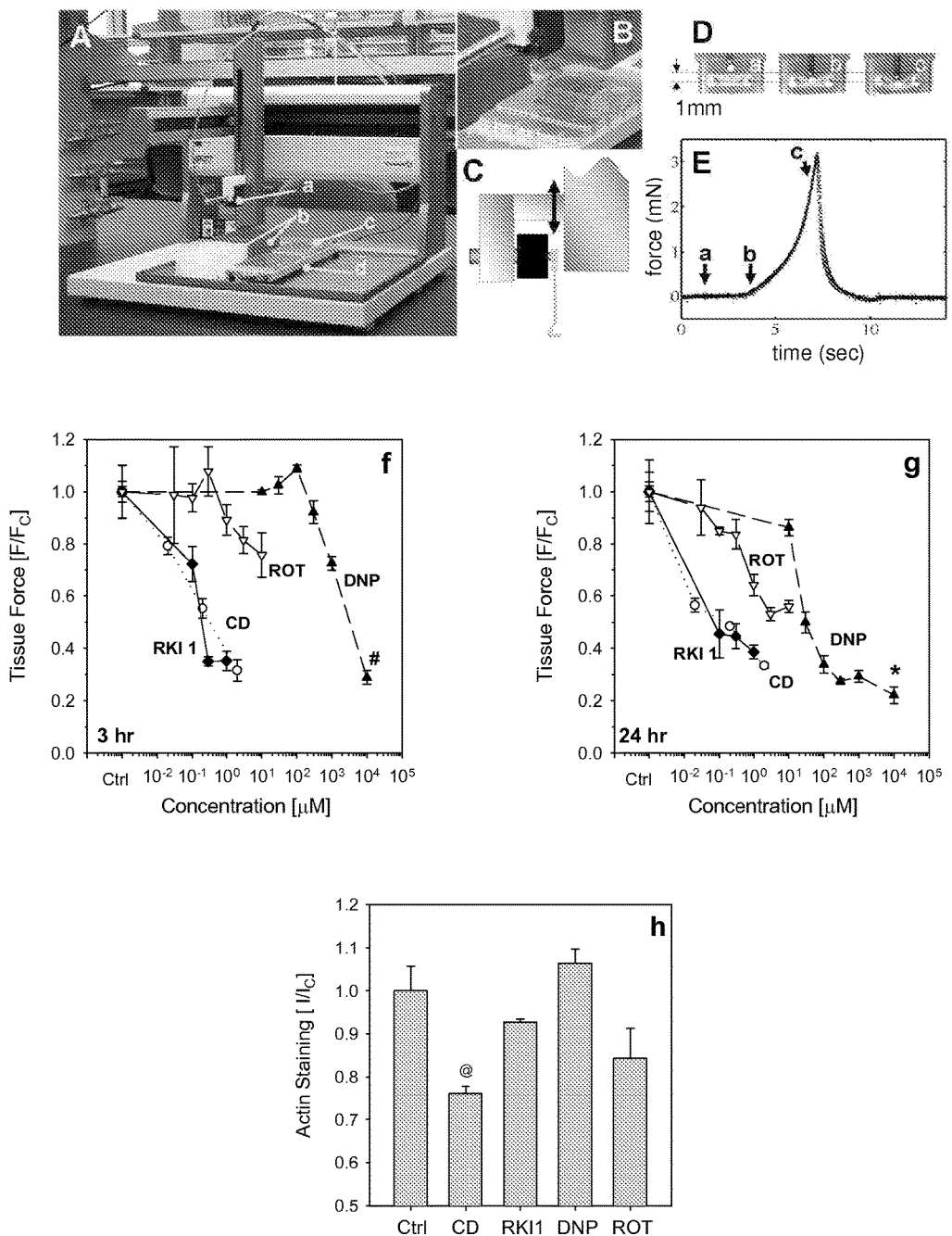
FIGS. 5(f and g) are graphs showing that Rho kinase inhibitor 1 (RKI1), Cytochalasin D (CD), rotenone (ROT), and 2,4-dinitrophenol (DNP) dose-dependently reduced HTC contractile force. HTCs were preconditioned, then treated with varying concentrations of the four drugs as indicated. Forces were measured at 3 (f) and 24 hr (g). Force measurements were expressed relative to control, medium treated, HTCs ($F_c$). Data show mean and SEM of predominately 4, with several 2 and 3, replicates; Z-factor>0.44 (#) and 0.59(*).
Figure 5:
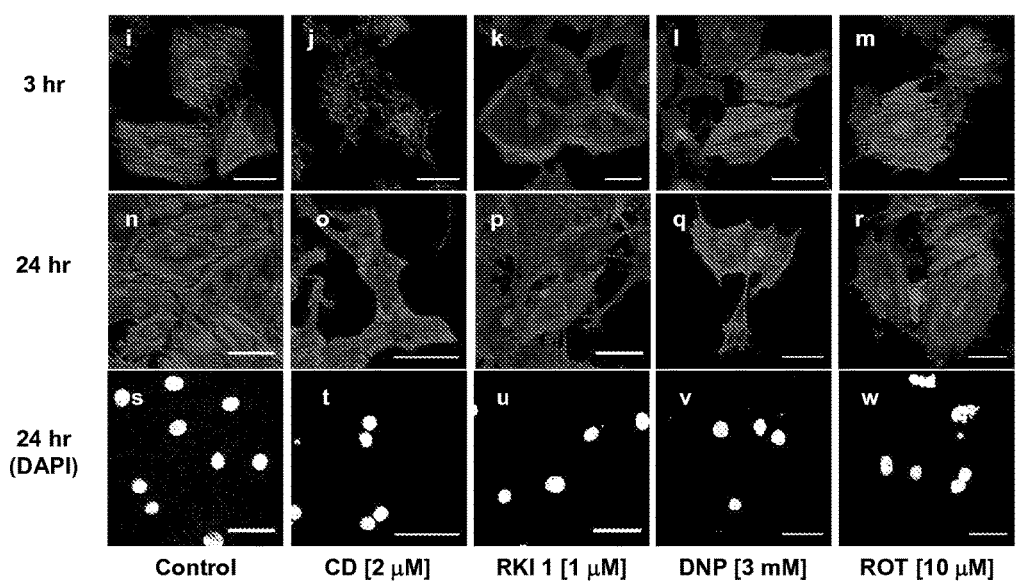

In this study, four different classes of compounds with well-known targets and biological effects were added to the HTCs and their dose-dependent effects on HTC mechanics were determined. Treating HTC for 3 and 24 hours with rho kinase inhibitor (RKI), H-1152 and cytochalasin D (CD), which disrupts actin polymerization, dose-dependently reduced tissue force (both $EC_{50} \approx 0.1$ μM, FIG. 5f, 3 hr). Dinitrophenol (DNP), an uncoupler of mitochondrial membrane potential (MMP) also reduced tissue force but at ~10,000-fold higher concentrations than H-1152 or CD. Rotenone (ROT), a widely used insecticide with well-known toxic effects on mammalian cells, also reduced tissue force. Because of its low solubility in aqueous medium (~100 μM), we were not able to further increase ROT concentrations. Generally 24 hours incubation of all compounds enhanced their effects on force reduction (FIG. 5g). In particular, the DNP's $EC_{50}$ dropped from 1.3 mM to 20 μM by the additional ~20 hours of incubation. However, the highest concentrations of DNP, CD, and H-1152 did not further reduce tissue force at 24 hours which suggests that these doses achieved maximum effects in 3 hours. These results demonstrate that each compound was effective at reducing tissue force.

Tissue force is maintained through the integrity of the cellular cytoskeleton, especially actin and myosin. To quantify amount of F (filamentaous)-actin in the HTCs treated with the compounds, the HTCs were stained with Alexa 546 conjugated phalloidin. The intensity of Alexa-phalloidin was measured by a plate reader and F-actin content in HTCs treated with CD (2 μM) was significantly reduced (FIG. 5h). This is in agreement with our previous report that CD mediated reduction in tissue force was due to the loss of intact F-actin. However, force reductions by H1152 and DNP were not related to the loss of F-actin. Alexa-phalloidin labeling in these HTCs were comparable to controls. F-actin was also reduced by ROT treatment; however this result was inconclusive due to insufficient statistical significance. Microscopic analysis of phalloidin-stained cells treated with 2 μM CD exhibited extensive disruption of F-actin as early as 3 hours (FIG. 5j). By 24 hours, short F-actins were re-distributed within less-spread (FIG. 5o) and binuclear (FIG. 5t) cells.

RKI, DNP, and ROT did not dramatically affect F-actin morphology (FIG. 5k-m). RKI treated cells did exhibit limited membrane ruffling and reduced phalloidin staining in the central region of the cells (FIG. 5c). Confluency of cells treated with DNP (FIG. 5q) and ROT (FIG. 5r) for 24 hours were less than that of control (FIG. 5n). Noticeable nuclear fragmentation in ROT-treated cells indicated the induction of apoptosis (FIG. 5w). While these morphological changes can be recognized in these images manually, automated quantitative HTP analysis will require sophisticated analysis algorithms.

Figure 6:
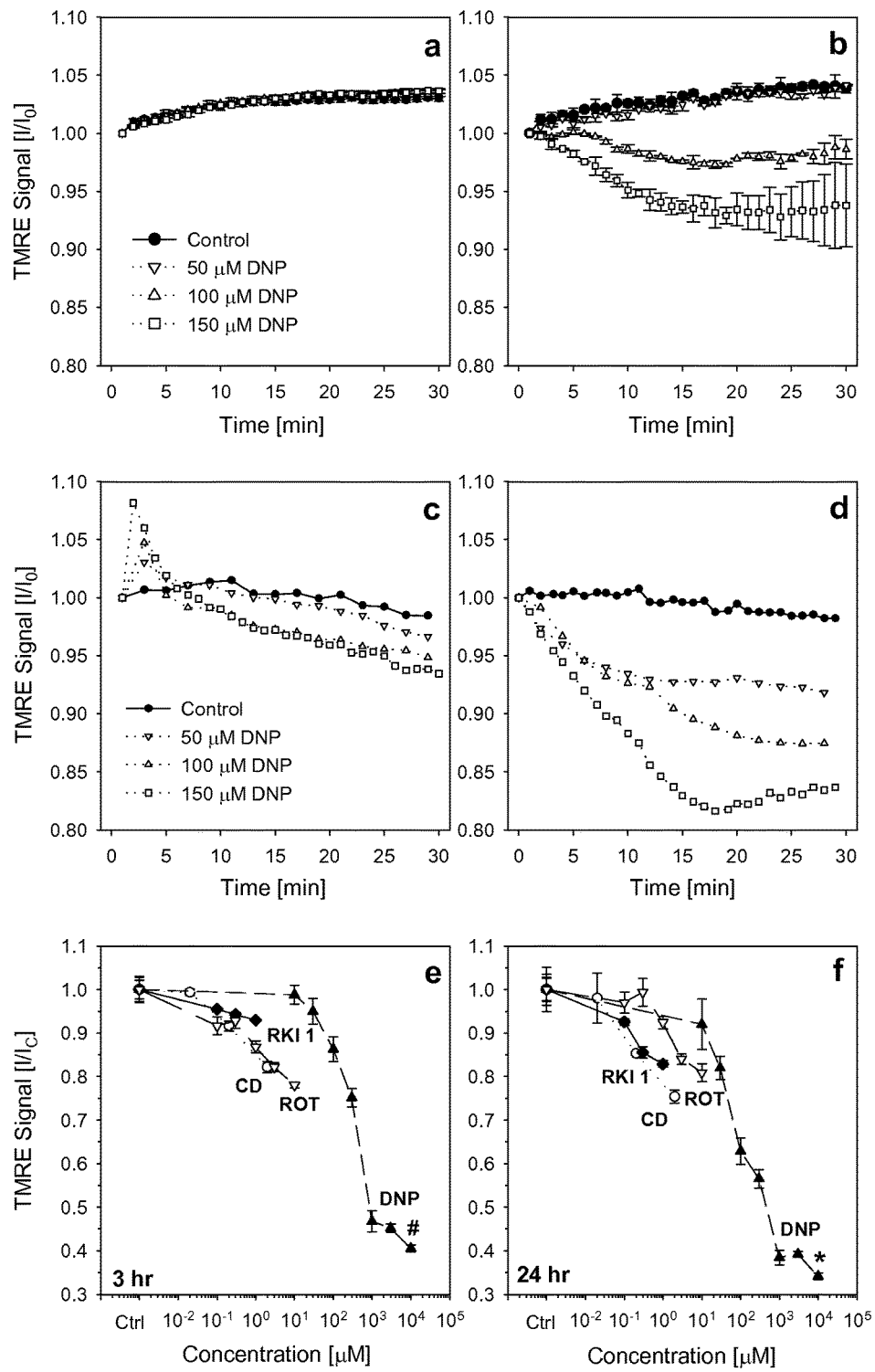
FIGS. 6(e and f) are graphs showing that DNP dose-dependently uncoupled HTC mitochondrial potential. HTCs preloaded with TMRE (100 nM for 30 min) were treated with varying concentrations of CD, RKI1, DNP, and ROT. TMRE fluorescence signal was measured using a plate reader at 3 (a) and 24 (b) hr post treatment. Signal intensity was expressed relative to the control, medium treated, HTCs ($I_c$). The mean and SEM of 4 (several with 2 or 3) replicates are shown; Z-factor>0.64 (#) and 0.46 (*).

To further identify the underling mechanism(s) by which the compounds reduced tissue force, changes in mitochondrial potential were quantified using the biological dye tetramethylrhodamine ethyl ester (TMRE). TMRE is cationic and accumulates in the mitochondria as a function of MMP. Initial studies of DNP treated monolayers, in 96-well plates, and HTCs, showed that DNP-mediated reduction of TMRE labeling was not detectable in monolayers (FIG. 6a), on a plate reader, but was readily quantifiable in HTCs (FIG. 6b). More detailed investigation of DNP's effect on TMRE accumulation using confocal microscopy improved signal detection in both monolayers and HTCs (FIG. 6 c, d). However, HTC experiments still showed superior sensitivity in detecting the dose-dependent MMP reduction by DNP over cell-monolayer experiments. Considering the superior sensitivity of signal detection, improved signal-to-noise ratio of the data, and the compatibility of plate reader scanning to HTP applications, we used HTCs for studying the compounds' effects on MMP.

DNP treatments for 3 hours uncoupled MMP and dose-dependently reduced TMRE signals (FIG. 6e) with $EC_{50}$ ~340 μM. Incubation for an additional 21 hours only slightly enhanced DNP's effect and further reduced $EC_{50}$ to ~95 μM (FIG. 6f). This 3.6 fold reduction in TMRE $EC_{50}$ by 24 hours treatment was significantly less than the 65-fold reduction in $EC_{50}$ of DNP's effect on tissue force (FIG. 5f, g). This difference suggests that DNP's rapid MMP uncoupling resulted in a gradual reduction in cellular contractile activity. Since actin polymerization and myosin-dependent cellular contraction require ATP, one expects the rapid loss in MMP would reduce ATP production in the mitochondria and thus reduce cellular contractility. This time-delayed reduction in tissue force indicates the existence of an intracellular ATP reserve and/or the cells' ability to up-regulate glycolysis for producing ATP. Up-regulation of ATP production via glycolysis has been reported in tumor cells and some cell lines. CD, RKI, and ROT treatment reduced mitochondrial membrane potential but the extents to which they reduced MMP were limited to 10-20% (FIG. 6e, f).

Figure 7:
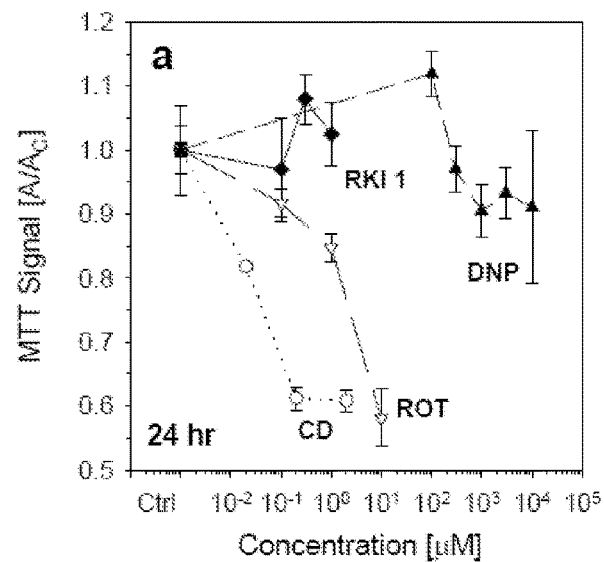
FIG. 7(c-f) are graphs showing phenotypic profiles used to screen the compounds. Physiology data, i.e., tissue force (Force), mitochondrial potential (Mit. Pot.), and MTT conversion (MTT Conv.), at 24 hr for each compound was normalized to the maximal effect (by one of the four compounds) and then fitted with a linear or Four Parameter Logistic function (lines). A profile that decreases from 1 to 0 indicates that the compound has a maximal negative effect on that specific physiology. The phenotypic profiles simplify compound selection process by making evident that RKI1 is the optimal candidate compound since it effectively reduced tissue force (from 1 to 0) while exhibiting minimal uncoupling activity (mitochondrial toxicity) and reduction in MTT conversion (cytotoxicity).
Figure 7:
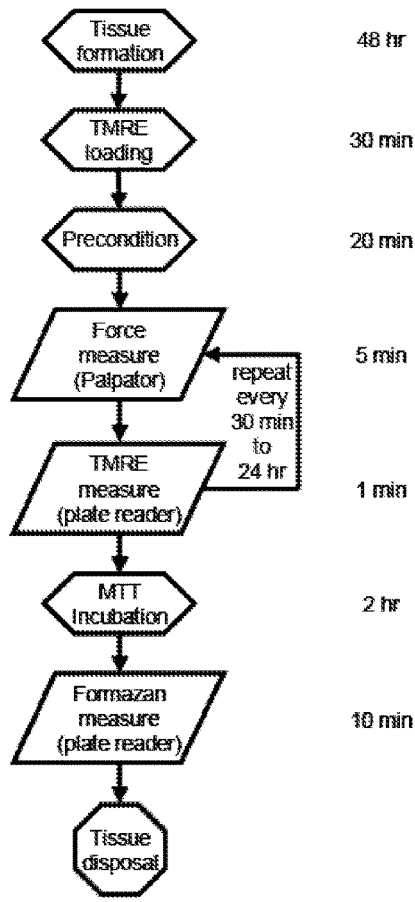
Figure 7:
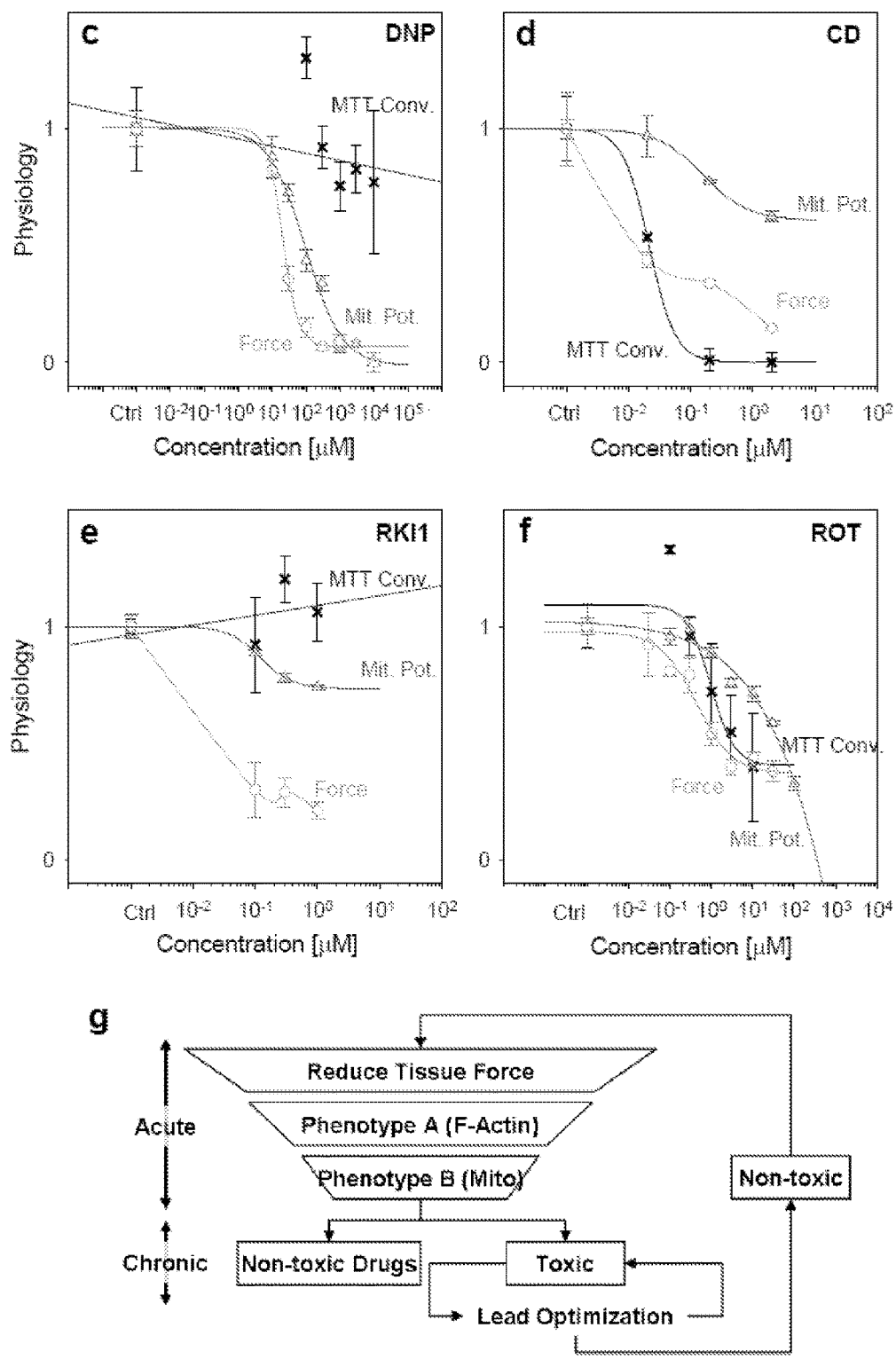

Finally to measure the compounds' effects on cellular viability, the assay using 3-(4,5-Dimethylthiazol-2-yl)-2,5-diphenyltetrazolium bromide (MTT) was performed. In cells, the yellow MTT is converted to a purple colored formazan by succinate dehydrogenase and this change can be quantified by light absorbance between 500-600 nm was quantitatively recorded using the plate reader. Treatments for 3 hours did not result in a significant loss in viability, as detected by the MTT assays (results not shown). CD and ROT treatment for 24 hours showed dose-dependent reduction in HTCs' viability (FIG. 7a). Both 0.2 and 2 µM CD treatments reduced MTT signal by 40%. The observed level of CD toxicity was similar to the reported $LD_{50}$ of 5-30 µM in human epidermoid cell lines. Higher ROT concentration, 10 µM, was required to reduce MTT signal by 40% (FIG. 7a). This level of ROT toxicity is slightly higher than the 25% toxicity previously reported in HepG2 cells. RKI and DNP treatments for 24 hours did not affect MTT signal.

HTC force measurement, TMRE quantitation, and MMT assay were performed on the same HTC samples. A diagram of the integrated screening workflow (FIG. 7b) shows the efficiency in obtaining high-content physiological information using HTCs. The results were summarized as panels of phenotypic profiles that represent the physiological impact of the compounds (FIG. 7c-f). DNP, CD, and RKI were all very effective at reducing HTC force. However, DNP exhibited extensive uncoupling effect of mitochondrial potential (FIG. 7c) while CD was highly toxic (FIG. 7d). ROT, on the other hand, had a moderate negative impact on HTC force, mitochondrial potential, and viability (FIG. 7f). RKI was identified to be the best candidate compound with force-reducing $EC_{50}$ of 0.1 µM with limited mitochondrial and viability toxicity. This result was not surprising since RKIs are well known to be cardioprotective, non-toxic, compounds that can effectively reduce tissue stiffness. Further, an RKI drug, Fasudil, has recently completed phase II clinical study for atherosclerosis and hypercholesterolemia.

In summary, the inventors have demonstrated how HTCs can be used to screen for compounds that can reduce tissue contractile force and yet have minimal effects on mitochondrial functions and cellular viability. With this HTC-based screening system we were able to study cellular physiology and quantify mechanical force within a more natural microenvironment, i.e., embedded in a three-dimensional matrix structure, as compared to two-dimensional cultures.

Further, the compact and multi-layered arrangement of cells in the HTCs greatly increased the detection limit and the signal-to-noise ratio of fluorescent assays. With Z-factors ranging from 0.44 to 0.85, the high accuracy and robustness of the assays will facilitate the incorporation of HTCs into existing HTP screening workflow.

In summary, the inventors provide a high throughput system utilizing a three dimensional tissue model for performing cell-based assays. The foregoing description is considered as illustrative only of the principles of the invention. Further, since numerous modifications and changes may readily occur to those skilled in the art, it is not intended to limit the invention to the exact construction and operation shown and described, and accordingly, all modifications and equivalents are considered as falling within the scope of the invention.

I claim:

1. A method of detecting the response of a tissue to an agent comprising:
   (a) contacting a three-dimensional bio-artificial tissue with an agent, the bio-artificial tissue comprising cells and having an extracellular matrix polymerized therearound, the bio-artificial tissue formed, and suspended on a scaffold support, and overlaying the support without a fastener to facilitate tissue adhesion, the scaffold support being positioned above the bottom of a well with a space between the bio-artificial tissue and the bottom of the well,
   (b) without removing the bio-artificial tissue from the well, performing a cell-based assay on the bio-artificial tissue in the well, wherein the assay produces an indicator of a physiologic response of the tissue to the agent, and the indicator is suitable for optical detection, and
   (c) optically detecting a level of the indicator in the well, wherein the level of the indicator is indicative of the response of the bio-artificial tissue to the agent.

2. The method of claim 1, wherein the cells are selected from the group consisting of a muscle cell, a non-muscle cell, an endothelial cell, and a cardiac cell.

3. The method of claim 1, wherein the well is a well of positioned within a multi-well plate.

4. The method of claim 3, wherein the multi-well plate comprises from 2 to 10,000 wells.

5. The method of claim 1, wherein the scaffold support is a wire frame and the bio-artificial tissue overlays and is attached at a perimeter to a the wire frame.

6. The method of claim 5, wherein the wire is stainless steel wire.

7. The method of claim 1, wherein the cells comprise cells known to be involved in a disease.

8. The method of claim 1, wherein the indicator is a colorimetric or a fluorometric indicator.

9. The method of claim 1, wherein the level of the indicator is detected using a microscope.

10. The method of claim 1, wherein the indicator is a radioactive label.

11. The method of claim 10, wherein the level of the indicator is detected using a scintillator.

12. The method of claim 1, wherein the level of the indicator is detected using a multi-well plate reader.

13. The method of claim 1, wherein the assay is selected from the group consisting of cell proliferation assays, cell death assays, apoptosis assays, protein expression assays, gene expression assays, enzymatic assays, and cell signaling assays.

14. The method of claim 1, wherein the agent is a candidate pharmaceutical.

15. The method of claim 1, wherein the method is a high throughput screening method.

16. The method of claim 1, further comprising performing a mechanical measurement of the contacted bio-artificial tissue to determine a change in a mechanical property.

17. The method of claim 1, wherein the bio-artificial tissue comprises cardiac cells and fibroblasts.

18. A method of detecting the response of a tissue to an agent comprising: (a) contacting a three-dimensional bio-artificial tissue with an agent, the bio-artificial tissue comprising cells embedded in an extracellular matrix without the use of a microcarrier material, the bio-artificial tissue formed on and overlaying a scaffold support without a fastener to facilitate tissue adhesion, the scaffold support being positioned above the bottom of a well, (b) performing a cell-based assay on the bio-artificial tissue, wherein the assay produces an indicator of a physiologic response of the tissue to the agent, and (c) detecting a level of the indicator in the well, wherein the level of the indicator is indicative of the response of the bio-artificial tissue to the agent, and the indicator is suitable for optical detection.

19. The method of claim 18, wherein the bio-artificial tissue is attached at a perimeter to a wire frame, the wire frame coupled to the scaffold support.

20. The method of claim 1, wherein the scaffold has at least two parallel, spaced apart members, each positioned within the well and disposed above and substantially parallel to the bottom of the well; and having at least one leg for supporting the scaffold above the bottom of the well.

21. The method of claim 1, wherein the scaffold has at least one elongate member, and is disposed within the well above and substantially parallel to the bottom of the well, and having at least one leg for supporting the scaffold above the bottom of the well.

22. The method of claim 1, wherein the bio-artificial tissue is suspended from the scaffold support with a space between the bio-artificial tissue and the bottom of the well.

23. A method for screening the effects of a pharmaceutical agent on a tissue, comprising: a) contacting an agent with a plurality of three-dimensional bio-artificial tissues suspended from and overlaying a plurality of scaffolds without a fastener to facilitate tissue adhesion to the scaffold; each of the plurality of scaffolds positioned within a well of a multi-well plate without any mesh covering the bottom of the well to provide an array of locations, wherein the agent contacting each bio-artificial tissue is the same or different; b) without removing the bio-artificial tissues from the wells, performing a cell-based assay on each bio-artificial tissue in the well, wherein the assay produces an indicator of a physiologic response of the tissue to the agent, and the indicator is suitable for optical detection, and c) optically detecting a level of the indicator in each well, wherein the level of the indicator is indicative of the response of the bio-artificial tissue to the agent in each well.

\* \* \* \* \*